(12) United States Patent
Dunn et al.

(10) Patent No.: US 6,207,829 B1
(45) Date of Patent: Mar. 27, 2001

(54) PROCESS FOR PREPARATION OF PYRAZOLO[4,3-D]PYRIMIDIN-7-ONES AND INTERMEDIATES THEREOF

(75) Inventors: Peter James Dunn; Philip Charles Levett, both of Sandwich (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/415,440

(22) Filed: Oct. 8, 1999

(30) Foreign Application Priority Data

Oct. 12, 1998 (GB) .................................................. 9822238

(51) Int. Cl.⁷ ...................... C07D 213/00; C07D 241/00; C07D 403/00; C07D 471/00; C07D 487/00
(52) U.S. Cl. .......................... 544/262; 544/336; 544/360; 544/366; 546/1; 548/364.1; 548/364.7; 548/371.4
(58) Field of Search .................................... 544/262, 336, 544/360, 366; 546/1; 548/364.1, 364.7, 371.4

(56) References Cited

FOREIGN PATENT DOCUMENTS

463756 * 6/1991 (EP) .
9849166 * 11/1998 (WO) .

* cited by examiner

*Primary Examiner*—Mukund J. Shah
*Assistant Examiner*—Sudhaker B. Patel
(74) *Attorney, Agent, or Firm*—Peter C. Richardson; Gregg C. Benson; B. Timothy Creagan

(57) ABSTRACT

A process is provided for the preparation of a compound of formulae (IA) (sidenafil) and (IB)

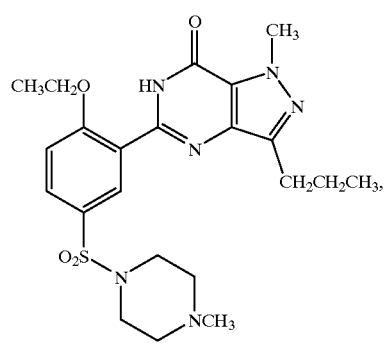

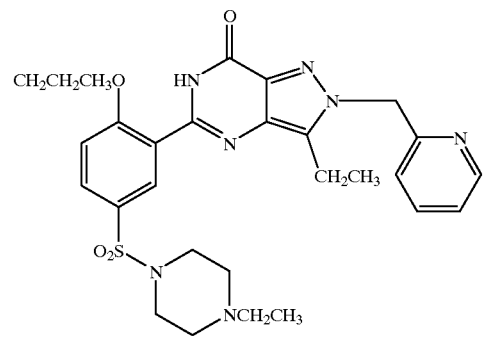

comprising reacting a compound of formula (IIA) and (IIB) respectively in the presence of ⁻OR, wherein R in the case of formation of compound (IA) is $CH_2CH_3$ and R in the case of formation of compound (IB) is $CH_2CH_2CH_3$, where X is a leaving group:

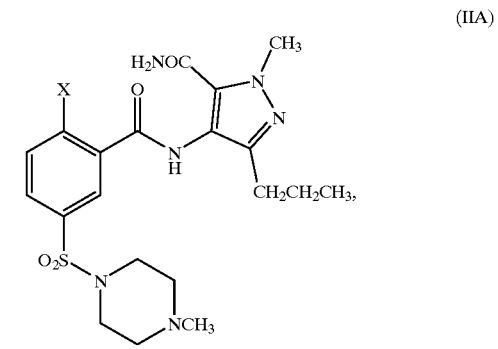

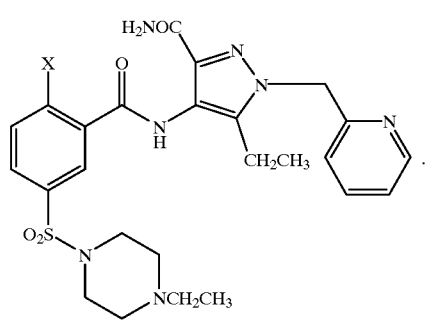

17 Claims, No Drawings

US 6,207,829 B1

PROCESS FOR PREPARATION OF PYRAZOLO[4,3-D]PYRIMIDIN-7-ONES AND INTERMEDIATES THEREOF

This invention relates to a process for the preparation of 1-[[3-(6,7-dihydro-1-methyl-7-oxo-3-propyl-1H-pyrazolo[4,3-d]pyrimidin-5-yl)-4-ethoxyphenyl]sulfonyl]-4-methylpiperazine(otherwise known as sildenafil or Viagra™), and 1-Ethyl-4-{3-[3-ethyl-6,7-dihydro-7-oxo-2-(2-pyridylmethyl)-2H-pyrazolo[4,3-d]pyrimidin-5-yl]-4-propoxyphenylsulphonyl}piperazine and key intermediates thereof.

1-[[3-(6,7-dihydro-1-methyl-7-oxo-3-propyl-1H-pyrazolo[4,3-d]pyrimidin-5-yl)-4-ethoxyphenyl]sulfonyl]-4-methylpiperazine (otherwise known as sildenafil) has been found to be particularly useful in the treatment of, inter alia, male erectile dysfunction (WO-A-94/28907), and a process for its preparation is disclosed in EP-A-O463756 (example 12) and Drugs of the Future 1997, 22(2): 138–143. An improved process for preparing sildenafil (over that of EPO463756) is disclosed in EP-A-O812845, with the characterising final step involving cyclisation under basic, neutral or acidic conditions to form sildenafil. A process for the preparation of 1-Ethyl-4-{3-[3-ethyl-6,7-dihydro-7-oxo-2-(2-pyridylmethyl)-2H-pyrazolo[4,3-d]pyrimidin-5-yl]-4-propoxyphenylsulphonyl}piperazine is disclosed in WO 98/49166 (example 5B).

The present inventors have now found a process for preparing sildenafil and 1-Ethyl-4-{3-[3-ethyl-6,7-dihydro-7-oxo-2-(2-pyridylmethyl)-2H-pyrazolo[4,3-d]pyrimidin-5-yl]-4-propoxyphenylsulphonyl}piperazine which has advantages over the aforementioned prior art processes.

According to the present invention there is provided a process for preparing a compound of formula (IA) and (IB)

(IA)

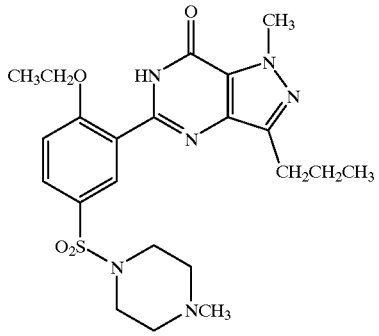

(IB)

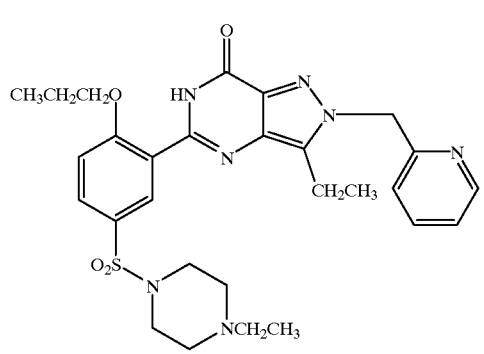

comprising reacting a compound of (IIA) and (IIB) respectively in the presence of ⁻OR, wherein R in the case of formation of compound (IA) is $CH_2CH_3$ and R in the case of formation of compound (IB) is $CH_2CH_2CH_3$, where X is a leaving group:

(IIA)

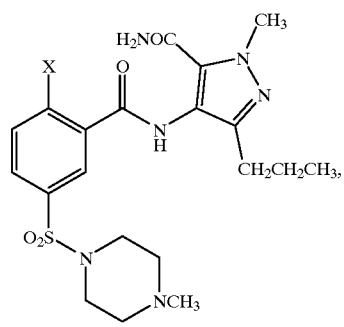

(IIB)

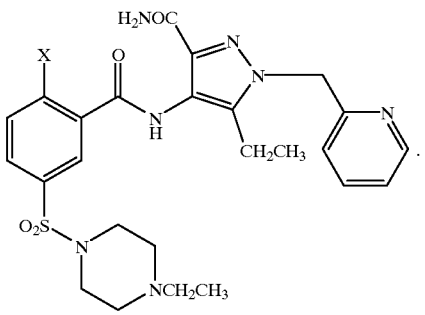

A particular advantage of the present process over that of the prior art is the elimination of steps by carrying out a substitution reaction and ring closure in 'one pot'.

The intermediates of general formula (IIA) and (IIB) form a further aspect of the invention.

A key intermediate of the general formula (IIIA) and (IIIB) (see schemes 1 and 2 hereafter) have been identified in various reactions showing that such reactions at least partially go via a pathway of cyclisation then nucleophilic substitution. Accordingly intermediates of general formula (IIIA) and (IIIB) form yet a further aspect of the invention (wherein X is a leaving group).

A further major intermediate of formula IVA and IVB have also been identified, suggesting that there is also nucleophilic substitution before cyclisation (and these intermediates, where novel, form a further aspect of the invention).

Thus the proposed reaction pathways for the formation of compounds (IA) and (IB) are as follows

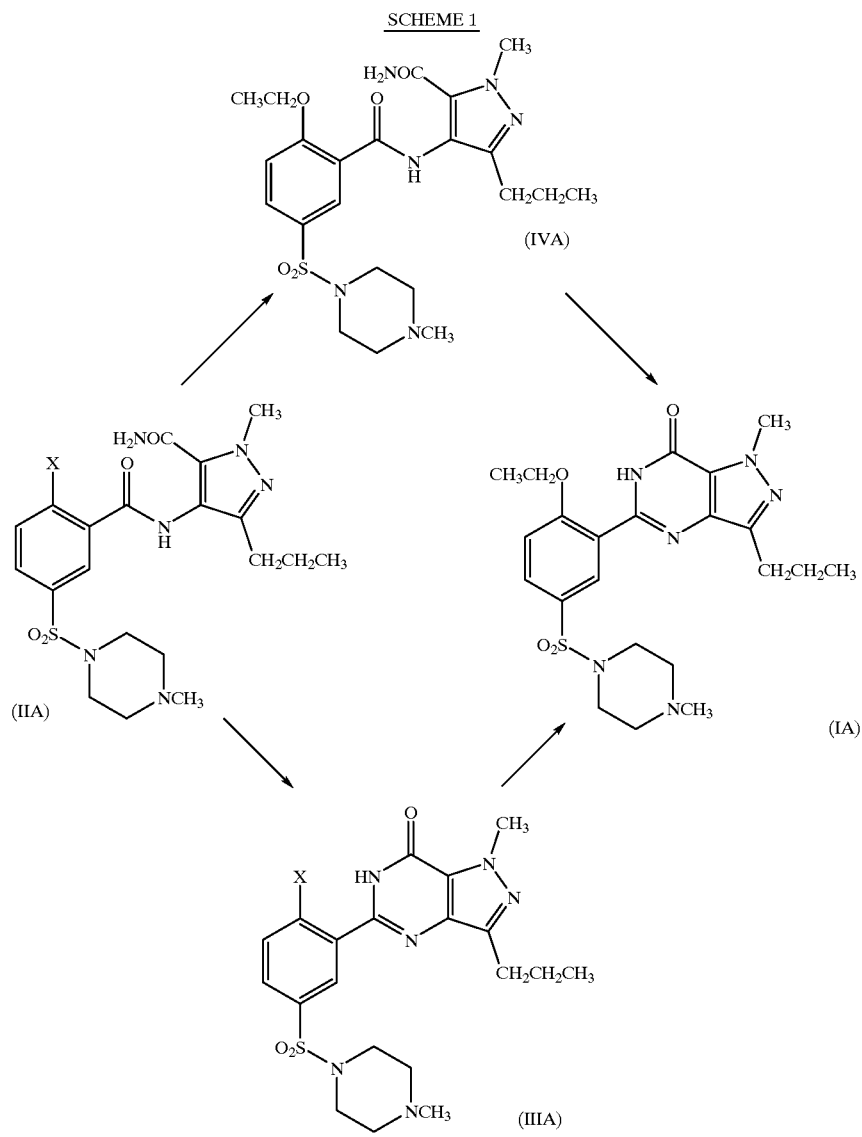

SCHEME 2

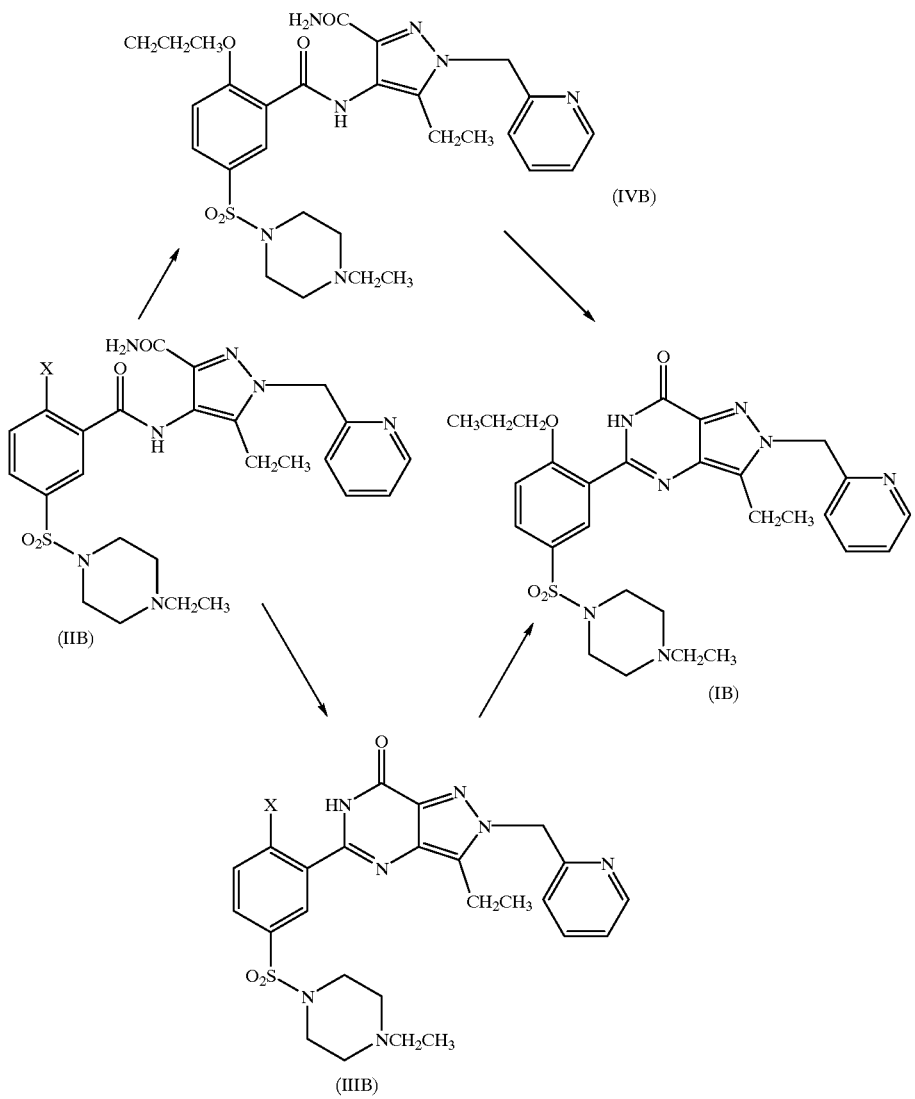

The relative proportion of intermediates formed is partially dependent on the nature of X (the leaving group).

Preferably X is selected from the group consisting of optionally substituted arylsulphonyloxy, preferably phenylsulphonyloxy, more preferably a para substituted aryl (phenyl) such as by a $C_1$–$C_4$ alkyl group e.g. p-toluenesulphonyloxy; $C_1$–$C_4$ alkylsulphonyloxy e.g. methanesulphonyloxy; nitro or halo substituted benzenesulphonyloxy preferably para substituted e.g. p-bromobenzenesulfonyloxy or p-nitrobenzenesulphonyloxy; $C_1$–$C_4$ perfluoroalkylsulphonyloxy e.g. trifluoromethylsulphonyloxy; optionally substituted aroyloxy such as benzoyloxy; $C_1$–$C_4$ perfluoroalkanoyloxy such as trifluoroacetyloxy; $C_1$–$C_4$ alkanoyloxy such as acetyloxy; halo; diazonium; $C_1$–$C_4$ primary and secondary alkoxy such as methoxy; oxonium; perchloryloxy; quatenaryammonium $C_1$–$C_4$ alkylsulphonyloxy; halosulphonyloxy e.g. fluorosulphonyloxy and other fluorinated leaving groups; halonium; and diarylsulphonylamino e.g. ditosyl ($NTs_2$).

Suitably X is a halo (fluoro, chloro, bromo or iodo) or methoxy, and most suitably it is fluoro or chloro. The latter have been found to provide particularly good yields, and inexpensive commercially available starting materials (chloro and fluoro benzoic acid) can readily be used.

Herein $^-OCH_2CH_3$ and $^-OCH_2CH_2CH_3$ (disclosed in the first aspect of the invention) are referred to for convenience as $^-OR$. $^-OR$ can act as both a nucleophile (to displace the leaving group by nucleophilic substitution) and as a base (to bring about the cyclisation).

$^-OR$ can be generated in solution from, a salt ZOR (wherein Z is a cation) such as a metal salt. More particularly an alkali (such as sodium or potassium) or alkaline earth metal salt of $^-OR$ in a suitable solvent would give rise to $^-OR$ in solution. For example sodium ethoxide ($Na^+$ OEt) in a suitable solvent with intermediate (IIA) would form sildenafil. In another embodiment, $^-OR$ is formed insitu from ROH plus an auxiliary base (i.e. a base other than $^-OR$). However, in another system, ZOR could be used in the reaction system with an auxiliary base.

Preferred embodiments of the invention are:
1. the synthesis of compound (IA) by reaction of compound (IIA):

a) with ethanol and auxiliary base, optionally in an inert solvent;
b) with ZOEt and an auxiliary base in ethanol or an inert solvent or both;
c) with ZOEt and ethanol or an inert solvent or both. the synthesis of compound (IB) by reaction of compound (IIB):
d) with propanol and auxiliary base, optionally in an inert solvent;
e) with ZOPr and an auxiliary base, in propanol or an inert solvent or both;
f) with ZOPr, and propanol or an inert solvent or both.

As will be appreciated the solvent in which the reaction takes place can be ROH or an inert solvent (or a mixture of both). By inert solvent we mean a solvent which will not form a nucleophile under the reaction conditions or if a nucleophile is formed it is sufficiently hindered such that R does not substantially compete in the displacement reaction. When ROH is used as a source of $^-$OR, then a separate solvent is not essentially required but an (auxiliary) inert solvent (i.e. a solvent other than ROH) may be used as a co-solvent in the reaction.

Suitable solvents are as follows: ethanol (for IA), propanol (for IB) (n-propanol), a secondary or tertiary $C_4$–$C_{12}$ alkanol, a $C_3$–$C_{12}$ cycloalkanol, a tertiary $C_4$–$C_{12}$ cycloalkanol, a secondary or tertiary ($C_3$–$C_7$ cycloalkyl) $C_2$–$C_6$ alkanol, a $C_3$–$C_9$ alkanone, 1,2-dimethoxyethane, 1,2-diethoxyethane, diglyme, tetrahydrofuran, 1,4-dioxan, toluene, xylene, chlorobenzene, 1,2-dichlorobenzene, acetonitrile, dimethyl sulphoxide, sulpholane, dimethylformamide, N-methylpyrrolidin-2-one, pyridine, and mixtures thereof.

A wide range of auxiliary bases can be used in the process of the invention. Typically the bases would not compete with $^-$OR in the nucleophilic substitution of X (i.e. they would be non nucleophilic) by suitably being sterically hindered. Preferred bases in accordance with the invention are selected from the group consisting of metal salts of a sterically hindered alcohol or amine such as a secondary or tertiary $C_4$–$C_{12}$ alkanol, a $C_3$–$C_{12}$ cycloalkanol and a secondary or tertiary ($C_3$–$C_8$ cycloalkyl)$C_1$–$C_6$ alkanol, a N-(secondary or tertiary $C_3$–$C_6$ alkyl)-N-(primary, secondary or tertiary $C_3$–$C_6$ alkyl)amine, a N-($C_3$–$C_8$ cycloalkyl)-N-(primary, secondary or tertiary $C_3$–$C_6$ alkyl)amine, a di($C_3$–$C_8$ cycloalkyl)amine or hexamethyldisilazane; metal salts of 1-methyl piperazine (especially for compound IA), 1-ethylpiperazine (especially for compound IB), and morpholine; 1,5-diazabicyclo[4,3,0]non-5-ene and 1,8-diazabicyclo[5,4,0]undec-7-ene; tertiary amines such as triethylamine; metal hydride, oxide, carbonate, and bicarbonate.

Preferably the metal of the salt of ZOR and the auxiliary base are independently selected from alkali metals (lithium, sodium, potassium, rubidium, caesium) or alkaline earth metals (beryllium, magnesium, calcium, strontium, barium). More preferably the metal is sodium or potassium.

Preferably the auxiliary base is selected from the group consisting of metal salts of a sterically hindered alcohol or amine such as a secondary or tertiary $C_4$–$C_{12}$ alkanol, a $C_3$–$C_{12}$ cycloalkanol and a secondary or tertiary ($C_3$–$C_8$ cycloalkyl)$C_1$–$C_6$ alkanol, a N-(secondary or tertiary $C_3$–$C_6$ alkyl)-N-(primary, secondary or tertiary $C_3$–$C_6$ alkyl)amine, a N-($C_3$–$C_8$ cycloalkyl)-N-(primary, secondary or tertiary $C_3$–$C_6$ alkyl)amine, a di($C_3$–$C_8$ cycloalkyl)amine or hexamethyldisilazane; 1,5-diazabicyclo[4,3,0]non-5ene and 1,8-diazabicyclo[5,4,0]undec-7-ene; metal hydride, oxide, carbonate and bicarbonate.

More preferably still, the auxiliary base is selected from the sterically hindered bases of the previous paragraph (i.e. all of them except the metal hydride, oxide, carbonate and bicarbonate).

Most preferably the auxiliary base is the metal salt of a tertiary $C_4$–$C_6$ alcohol such as the alkali or alkaline earth metal salts (e.g. Na/K) of t-butanol or t-amyl alcohol.

To maximise yields, it is further preferred that at least one molecular equivalent (suitably one and a half equivalent) of auxiliary base and $^-$OR are used in accordance with the invention. If $^-$OR also functions as a base then preferably at least two equivalents, (more preferably three equivalents) of $^-$OR are present. Thus for example in preferred embodiments (a) to (f) above, preferably there is at least 2 equivalents of auxiliary base and at least one equivalent of EtOH or PrOH (a and d respectively), preferably at least 1 equivalent of auxiliary base and at least 1 equivalent of ZOEt or ZOPr (b and e respectively) and preferably at least 2 equivalents of ZOEt or ZOPr (c and f respectively). These are equivalents with respect to the molar quantities of IIA or IIB.

The nature of the leaving group (X) may influence the reaction pathway. For example with reference to scheme 1 for compound (IA), when X=F the reaction mostly proceeds via the intermediate illustrated by (IVA) but when the X=Cl the pathway shifts more towards the intermediate of (IIIA), and when X=OCH$_3$ there is more of the formula (IIIA) intermediate formed than the formula (IVA) type intermediate. However, formation of the final compound of formulae (IA) and (IB) from the intermediate formulae (IIIA) and (IIIB) respectively can be encouraged by using a higher temperature and allowing more time for formation of the final product.

Preferably the general reaction is carried out at from 50° C. to 170° C. Thus where X=F, the reaction temperature could be anything from about 50° C., preferably 60° C. upward and the rate of formation of the final product would be very good. For X=Cl, preferably a temperature of 60 to 170° C., more suitably at least 80° C. such as (80° C. to 110° C.) would increase the rate; and for X=OCH$_3$, preferably a temperature of at least 80° C., more suitably at least 110° C. (such as 110° C. to 140° C.) would increase the rate to the final product.

The compounds of general formula (IIA) and (IIB) may be obtained from readily available starting materials for example, by the route depicted in the following reaction schemes. Reaction scheme 3 is illustrated for compound (IA) and scheme 4 is illustrated for compound (IB).

With reference to scheme 3, the intermediate of formula (VIA) is formed from a substituted (i.e. group X) benzoic acid derivative by reaction with chlorosulphonic acid. Intermediate (VIA) is then reacted with N-methylpiperazine in the presence of a base, such as a tertiary amine, more particularly triethylamine and a suitable solvent such as acetone or water to form intermediate (VIIA).

(IIA) is formed by reaction of intermediate (VIA) and 4-amino-1-methyl-3-propyl-1H-pyrazole-5-carboxamide (compound IXA) in the presence of a coupling agent, such as 1-(3-dimethylaminopropyl)-3-ethyl carbodiimide hydrochloride and where desirable also in the presence of a base and/or an accelerator. In one example of a coupling system, the carboxylic acid function of (VIIA) is first of all activitated using about a 5% excess of a reagent such as N,N-carbonyldimidazole (as coupling agent) in a suitable solvent, e.g. ethyl acetate, at from about room temperature to about 80° C., followed by reaction of the intermediate imidazolide with (IXA) at from about 20 to about 60° C. In another example, intermediate (VIIA) could be coupled to the pyrazole (IXA) in the presence of 1-hydroxybenzotriazole, triethylamine and 1-(3-dimethylaminopropyl)-3-ethyl-carbodiimide hydrochloride.

Compound (IXA) is formed by reducing 1-methyl-4 nitro-3-propyl-1H-pyrazole-5 carboxamide (VIIA) such as by hydrogenation in the presence of 5% palladium on charcoal.

Compound (IB) (scheme 4) can be formed in an analogous fashion to that of compound (IA). More particularly, intermediate (VIIB) is prepared by reacting (VIA) with N-ethylpiperazine; and intermediate (IIB) is formed by coupling intermediate compounds (VIIB) and (IXB).

SCHEME 3

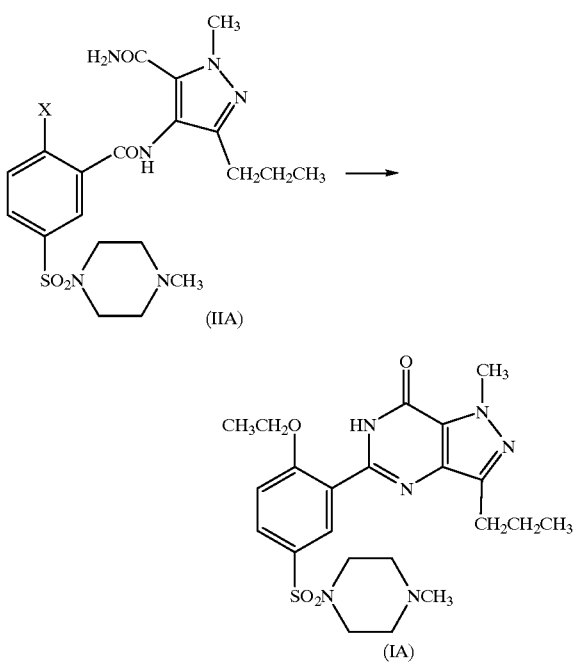

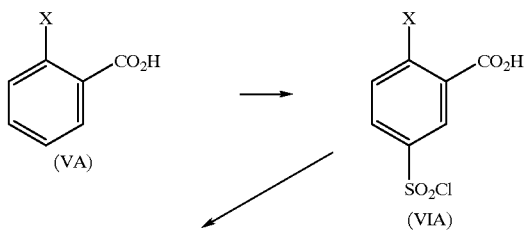

SCHEME 4

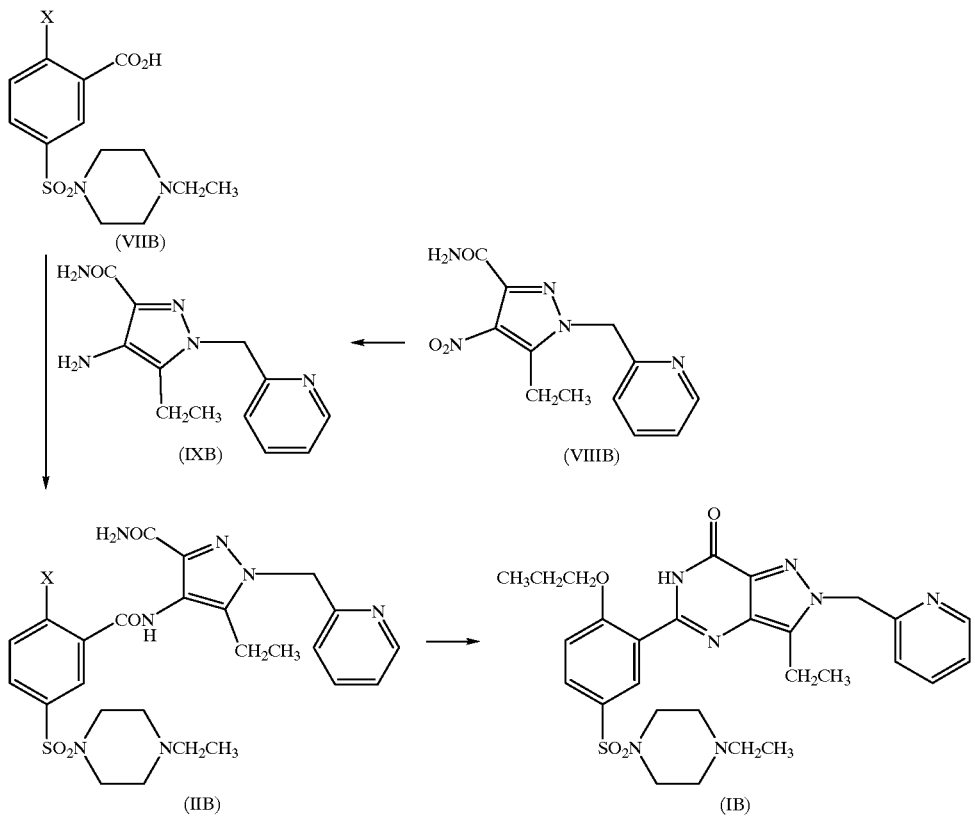

The intermediates of general formulae (VIIA) and (VIIB) are novel and form a further aspect of the invention (wherein X is as defined hereinbefore)

The invention will now be described by way of example only with reference to the following examples.

Example 1

(1a) 5-Chlorosulphonyl-2-fluorobenzoic acid (Compound VIA X=F)

Commercially available 2-fluorobenzoic acid (75 g, 0.54 Mol) was added to chlorosulphonic acid (320 g) over 15 minutes, stirred for 30 minutes then heated to 90° C. for 4½ hrs. Once cool, the reaction was quenched onto ice/water (1.5 kg/324 ml) and granulated for 1 hr. The precipitated product was filtered, water washed and dried at 50° C. under vacuo to give the title compound (99.7 g, 78.1%) as a white solid.

(1b) 2-Fluoro-5-(4-methyl-1-piperazinylsulphonyl) benzoic acid (Compound VIIA, X=F)

A solution of 5-chlorosulphonyl-2-fluorobenzoic acid (47.72 g, 0.2 mol) in acetone (250 ml) was added to a mixture of N-methylpiperazine (22.04 g, 0.22 mol) and triethylamine (24.29 g, 0.24 mol) and the reaction was stirred at ambient for three hours. The mixture was filtered, the resulting solid was recrystallised from water to afford the title compound (14.63 g, 24.2%) as a white solid. δ (DMSO): 2.30 (3H, s), 2.58 (4H, m), 2.95 (4H, m), 7.52 (1H, m), 7.90 (1H, m), 8.10 m/z (Found: 303 [M+H]$^+$, 100%, $C_{12}H_{16}FN_2O_4S$ requires 303).

(1c) 4-Amino-1-methyl-3-propyl-1H-pyrazole-5-carboxamide

A stirred suspension of 1-methyl-4-nitro-3-propyl-1H-pyrazole-5-carboxamide (EP-A-0463756; 237.7 g, 1.12 mol) and 5% palladium on charcoal (47.5 g) in ethyl acetate (2.02 l) was hydrogenated at 344.7 kPa (50 psi) and 50° C. for 4 hours, when the uptake of hydrogen was complete. The cool reaction mixture was filtered, then the filter pad washed with ethyl acetate, the combined filtrate and washings thus furnishing an ethyl acetate solution of the title compound (EP-A-0463756) which was of sufficient purity to use directly in the next stage of the reaction sequence.

(1d) 4-[2-Fluoro-5-(4-methyl-1-piperazinylsulphonyl) benzamido]-1-methyl-3-propyl-1H-pyrazole-5-carboxamide.(Compound IIA, X=F)

4-amino-1-methyl-3-propyl-1H-pyrazole-5-carboxamide (1.27 g, 6.94 mmol) was added to a suspension of 2-fluoro-5-(4-methyl-1-piperazinylsulphonyl)benzoic acid (2.0 g, 6.94 mmol), triethylamine (0.70 g, 6.92 mmol), 1-(3-dimethylaminopropyl)-3-ethylcarbodiimide hydrochloride (1.33 g, 6.94 mmol) and 1-hydroxybenzotriazole (0.94 g, 6.96 mmol) in a mixture of ethyl acetate (20 ml) and dichloromethane (20 ml). The reaction mixture was stirred for 12 hours at ambient temperature. The reaction mixture was stripped down to an oil and purified using column chromatography (flash silica, 30:70, methanol:ethyl acetate). The title compound of preparation was further purified by dissolving in dichloromethane and washing with saturated sodium bicarbonate solution. The organic solution was stripped down under vacuum to produce a solid which was dried (40° C.) to afford the title compound (2.1 g, 64.8%) as a white solid.

m.p. 210–212° C. Found: C, 51.15; H, 5.81; N, 17.90. $C_{20}H_{27}FN_6O_4S$ requires C, 51.49; H, 5.83; N, 18.01. δ (CDCl$_3$): 0.95 (3H, t), 1.62 (2H, m), 2.30 (3H, s), 2.50 (6H, m), 3.10 (4H, m), 4.10 (3H, s), 7.41 (1H, m), 8.00 (2H, m), 8.50 (1H, m). m/z (Found: 467.18909 ([M+H]$^+$, 37%), $C_{20}H_{28}N_6O_4SF$ requires 467.1890).

(1e) 1-[[3-(6,7-dihydro-1-methyl-7-oxo-3-propyl-1H-pyrazolo[4,3-d]pyrimidin-5-yl)-4-ethoxyphenyl]sulfonyl]-4-methylpiperazine. (Compound IA)

Potassium t-butoxide (0.74 g, 6.60 mmol) was added to a suspension of the title compound of example (1d) (1.00 g, 2.20 mmol) in ethanol (5 ml) and the mixture was heated under reflux for 48 hours. The reaction mixture was stripped down to an oil and purified by dissolving in dichloromethane and washing with saturated sodium bicarbonate solution. Hexane was added to the organic solution over 10 minutes, a precipitated solid filtered and dried to afford the title compound (1.1 g,100%) as a white solid. Recrystallisation of the title compound from ethyl acetate affords a solid with m.p.184–186° C.

Found: C, 55.49; H, 6.35; N, 17.72. $C_{22}H_{31}N_6O_4S$ requires C, 55.58; H, 6.53; N, 17.68. δ (DMSO): 0.96 (3H, t), 1.30 (3H, t), 1.72 (2H, m), 2.13 (3H, s), 2.36 (4H, m), 2.72 (2H, t), 2.90 (4H, m), 4.18 (5H, m), 7.32 (1H, d), 7.80 (2H, m). m/z (Found: 475.214800 ([M+H]$^+$, 100%). $C_{22}H_{31}N_6O_4S$. requires 475.212751).

The reaction went almost entirely via intermediate IVA, and went to completion in less than 48 hours.

Example 2

(2a) 2-Chloro-5-chlorosulphonylbenzoic acid (Compound VIA, X=Cl)

Commerically available 2-chlorobenzoic acid (80.0 g), (0.5 mol), was added portionwise to chlorosulphonic acid (320 g) with vigorous stirring. The reaction was heated to 95° C. for 6 hrs then cooled overnight to room temperature. The solution was quenched onto ice/water (1.5 kg/324 ml) and stirred for 15 min. The precipitated product was filtered, water washed and dried at 50° C. in vacuo, to give the title compound (111.1 g, 85.2%) as a white solid with m.p. 140° C. δ (CDCl$_3$): 7.42 (1H,m), 8.27 (1H,m), 8.75 (1H,m).

(2b) 2-Chloro-5-(4-methyl-1-piperazinylsulphonyl) benzoic acid (Compound VIIA, X=Cl)

The above compound was prepared by adding 2-chloro-5-chlorosulphonylbenzoic acid to 1.25 mol equivalent of N-ethylpiperazine in water (3 ml/g) under acidic conditions.

The title compound was then isolated as a solid (81.7%). Recrystallisation of the title compound from acetone: water affords a solid with m.p. 304–6° C., and the following characteristic data:

Found: C, 45.16; H, 4.71; N, 8.64. $C_{12}H_{15}ClN_2O_4S$ requires C, 45.21; H, 4.71; N, 8.79. δ (DMSO): 2.20 (3H, s), 2.50 (4H, m), 2.95 (4H, m), 6.75 (2H, m), 9.95 (1H, s), m/z (Found: 319 [M+H]$^+$, 100% $C_{12}H_{16}ClN_2O_4S$ requires 319).

(2c) 4-[2-Chloro-5-(4-methyl-1-piperazinylsulphonyl) benzamido]-1-methyl-3-propyl-1H-pyrazole-5-carboxamide. (Compound IIA, X=Cl)

4-Amino-1-methyl-3-propyl-1H-pyrazole-5-carboxamide (2.86 g, 15.68 mmol) (example 1c) was added to a suspension of 2-chloro-5-(4-methyl-1-piperazinylsulphonyl) benzoic acid (5.0 g, 15.68 mmol), triethylamine (1.59 g, 15.68 mmol), 1-(3-dimethylaminopropyl)-3-ethylcarbodiimide hydrochloride (3.00 g, 15.68 mmol), and 1-hydroxybenzotriazole (2.12 g, 15.68 mmol) in dichloromethane (50 ml). The reaction was stirred for 48 hours at ambient temperature, a further portion of 1-(3-dimethylaminopropyl)-3-ethyl carbodimide hydrochloride (1.00 g, 5.2 mmol) added and the reaction stirred for a further 48 hours at ambient temperature. The reaction mixture was washed with saturated sodium bicarbonate solution and ethyl acetate added to the separated organic solution over ten minutes. The mixture was stirred for ten minutes and a precipitated solid filtered, and dried to afford the title compound (6.0 g, 81%). m.p 105–107° C. δ (DMSO): 0.90 (3H, t), 1.60 (2H, m), 2.13 (3H, s), 2.40 (4H, m), 2.50 (2H, m), 2.95 (4H, m), 3.90 (3H, s), 7.30 (1H, s), 7.82 (4H, m), 10.0 (1H, s). m/z (Found: 505.140303 ([M+Na]$^+$, 28%). $C_{20}H_{27}ClN_6O_4SNa$. requires 505.140073).

(2d) 1-[[3-(6,7-dihydro-1-methyl-7-oxo-3-propyl-1H-pyrazolo[4.3-d]pyrimidin-5-yl)-4-ethoxyphenyl]sulfonyl]-4-methylpiperazine. (Compound IA)

Potassium t-butoxide (1.43 g, 12.75 mmol) was added to a suspension of the title compound of example 2(c) (2.00 g, 4.25 mmol) in ethanol (20 ml) and the mixture was heated under reflux for 48 hours. The pH of the reaction was adjusted to 6, using 1N hydrochloric acid, the precipitated solid filtered and dried to afford the title compound. Recrystallisation of the title compound from methyl isobutyl ketone afforded a solid with m.p 188° C. δ (CDCl$_3$): 1.01 (3H, t), 1.62 (3H, t), 1.88 (2H, m), 2.30 (3H, s), 2.50 (4H, m), 2.95 (2H, t), 3.13 (4H, m), 4.30 (3H, s), 4.39 (2H, q) 7.15 (1H, d), 7.82 (1H, m), 8.82 (1H, m). m/z (Found: 475.2127 ([M+H]$^+$, 100%). $C_{22}H_{31}N_6O_4S$. requires 475.212751).

Intermediate of formula IVA was prepared in accordance with EP-A-0812845, and intermediate of formula IIIA, X=Cl was prepared in accordance with example 2(e) herebelow. These intermediates were then used as markers for comparison of hplc samples taken from the reaction mixture during step, 2(d), in order to deduce the reaction path.

Intermediates IIIA (X=Cl) and IVA were observed (by hplc) in a ratio of about 20:80 respectively.

2(e): 1-[4-Chloro-3-(6,7-dihydro-1-methyl-oxo-3-propyl-1H-pyrazolo[4,3-d]pyrimidin-5-yl)phenylsulphonyl]-4-methylpiperazine, (Compound IIIA. X=Cl)

Potassium t-butoxide (0.24 g, 2.14 mmol) was added to a suspension of the title compound of example 2(c) (1.00 g, 2.12 mmol) in t-butanol (5 ml) and the mixture was heated under reflux for 120 hours. The reaction mixture was cooled and the precipitated solid was filtered and dried to afford the title compound (0.48 g, 50%) as a white solid m.p. 205–208° C. δ (DMSO): 0.90 (3H, t), 1.70 (2H, m), 2.13 (3H, s), 2.38 (4H, m), 2.68 (2H, t), 2.92 (4H, m), 4.10 (3H, s), 4.15 (1H, s), 7.60 (1H, m), 7.70 (1H, d), 7.85 (1H, m). m/z (Found: 465.1484 ([M+H]$^+$, 100%). $C_{20}H_{26}ClN_6O_3S$ requires 465.147564).

Example 3

(3a) 5-Chlorosulphonyl-2-methoxybenzoic acid (Compound VIA, X=OCH$_3$)

Commercially available 2-methoxybenzoic acid (15.2 g, 0.1 mol) was added portionwise to chlorosulphonic acid (52.43 g) over 30 min with ice cooling. Thionyl chloride (11.9 g, 0.1 mol) was added and the reaction stirred overnight. The reaction was quenched onto ice/water (250 g/65 ml) and the precipitated product granulated for 1 hr, filtered, water washed and oven dried to give the title compound (23.56 g, 93.9%) as a white solid with m.p. 138–140° C. δ (CDCl$_3$): 4.18 (3H, s), 7.23 (1H, d), 8.21 (1H, d), 8.78 (1H, s).

(3b) 2-Methoxy-5-(4-methyl-1-piperazinylsulphonyl) benzoic acid

The above compound was prepared by adding 5-chlorosulphonyl-2-methoxybenzoic acid to 1.1 mol equivalent of N-methylpiperazine and 1.2 mol equivalents of triethylamine in acetone (5 ml/g).

The title compound was then isolated by filtration, as a solid (79.1%), with the following characteristic data:

Found: C, 49.70; H, 5.76; N, 8.75. $C_{13}H_{18}N_2O_5S$ requires C, 49.68; H, 5.73; N, 8.92. δ (DMSO): 2.15 (3H, s), 2.35 (4H, m), 2.90 (4H, m), 3.90 (3H, s), 7.25 (1H, m), 7.10 (2H, m), m/z (Found: 315 [M+H]$^+$, 65% $C_{13}H_{19}N_2O_5S$ requires 315).

(3c) 4-[2-Methoxy-5-(4-methyl-1-piperazinylsulphonyl) benzamido]-1-methyl-3-propyl-1H-pyrazole-5-carboxamide. (Compound IIA, X=OCH$_3$)

A mixture of 2-methoxy-5-(4-methyl-1-piperazinylsulphonyl)benzoic acid (2.00 g, 6.36 mmol) and carbonyl diimidazole (1.03 g, 6.35 mmol) in dichloromethane (20 ml) was stirred for three hours at 30° C. 4-Amino-1-methyl-3-propyl-1H-pyrazole-5-carboxamide (1.16 g, 6.37 mmol) and triethylamine (0.64 g, 6.32 mmol) were added to the reaction mixture and stirred for 48 hours at ambient temperature. The reaction mixture was washed with saturated sodium bicarbonate solution, the separated organic solution stripped under vacuum to produce a solid which was dried (40° C.) to afford the title compound (2.74 g, 90%) as a white solid. m.p. 182° C.

Found: C, 52.42; H, 6.36; N, 17.31; $C_{21}H_{30}N_6O_5S$ requires C, 52.71; H, 6.32; N, 17.56. δ (DMSO): 0.90 (3H, t), 1.60 (2H, m), 2.12 (3H, s), 2.32 (4H, m), 2.42 (2H, t), 2.90 (4H, m), 3.90 (3H, s), 4.00 (3H, s), 7.32 (1H, s) 7.42 (1H, d), 7.80 (1H, s), 7.90 (2H, m), 9.70 (1H, s). m/z (Found: 479.2088 ([M+H]$^+$, 52%). $C_{21}H_{31}N_6O_5S$. requires 479.207665).

(3d) 1-[[3-(6.7-dihydro-1-methyl-7-oxo-3-propyl-1H-pyrazolo[4,3-d]pyrimidin-5-yl)-4-ethoxyphenyl]sulfonyl]-4-methylpiperazine. (Compound IA)

Potassium-t-butoxide (146 mg, 1.30 mmol) was added to a suspension of the title compound of step 3c (200 mg, 0.43 mmol) in ethanol (4 ml) and the mixture was heated under reflux for 120 hours. The reaction mixture was cooled and the pH of the reaction was adjusted to 6, using dilute hydrochloric acid. The precipitated solid was filtered and dried to afford the title compound (60 mg, 29%) as an off white solid with m.p. 187° C. δ (CDCl$_3$): 1.00 (3H, t), 1.62 (3H, t), 1.90 (2H, m), 2.22 (3H, s), 2.50 (4H, m), 2.95 (2H, t), 3.10 (4H, m), 4.30 (3H, s), 4.38 (2H, q), 7.15 (1H, d), 7.82 (1H, d), 8.82 (1H, s), 10.85 (1H, s). m/z (Found: 497.199635 [M$^+$, 100%]. $C_{22}H_{30}N_6O_4S$. requires 497.194695).

The following intermediate 3(e) was independently prepared and used as a marker, for hplc comparison of samples taken from the reaction mixture during step 3(d).

The intermediate of example 3(e) (IIIA, X=OCH$_3$) and intermediate IVA ware observed by hplc in a ratio of about 70:30 respectively.

(3e) 1-[3-(6.7-Dihydro-1-methyl-oxo-3-propyl-1H-pyrazolo[4.3-d]pyrimidin-5-yl)4-methoxy-phenylsulphonyl]-4-methylpiperazine (Compound IIIA. X=OCH$_3$)

Potassium t-butoxide (0.176 g, 1.57 mmol) was added to a suspension of the title compound of step 3c (0.75 g, 1.57 mmol) in t-butanol (5 ml) and the mixture was heated under reflux for 96 hours. The reaction mixture was cooled and the precipitated solid was filtered and dried to afford the title compound (0.33 g, 45.6%) as a white solid m.p. 182° C. δ (CDCl$_3$): 1.02 (3H, t), 1.88 (2H, m), 2.30 (3H, s), 2.50 (4H, m), 2.92 (2H, t), 3.10 (4H, m), 4.15 (3H, s), 4.30 (3H, s), 7.20 (1H, m), 7.95 (1H, d), 8.10 (1H, m).

Example 4

(4a) Ethyl 3-ethyl-1H-pyrazole-5-carboxylate

Ethanolic sodium ethoxide solution (21% w/w; 143 ml, 0.39 mol) was added dropwise to a stirred, ice-cooled solution of diethyl oxalate (59.8 ml, 0.44 mol) in absolute ethanol (200 ml) under nitrogen and the resulting solution stirred for 15 minutes. Butan-2-one (39 ml, 0.44 mol) was then added dropwise, the cooling bath removed, the reaction mixture stirred for 18 hours at room temperature and then for 6 hours at 40° C., then the cooling bath reintroduced. Next, glacial acetic acid (25 ml, 0.44 mol) was added dropwise, the resulting solution stirred for 30 minutes at 0° C., hydrazine hydrate (20 ml, 0.44 mol) added dropwise, then the reaction mixture allowed to warm to room temperature and maintained there over a period of 18 hours, before being evaporated under reduced pressure. The residue was partitioned between dichloromethane (300 ml) and water (100 ml), then the organic phase separated, washed with water (2×100 ml), dried (Na$_2$SO$_4$) and concentrated under reduced pressure to give the title compound (66.0 g). δ (CDCl$_3$): 1.04 (3H,t), 1.16 (3H,t), 2.70 (2H,q), 4.36 (2H,q), 6.60 (1H,s). LRMS: m/z 169 (M+1)$^+$.

(4b) 3-Ethyl-1H-pyrazol-5-carboxylic acid

Aqueous sodium hydroxide solution (10 M; 100 ml, 1.0 mol) was added dropwise to a stirred suspension of the title compound of example (4a) (66.0 g, 0.39 mol) in methanol and the resulting solution heated under reflux for 4 hours. The cool reaction mixture was concentrated under reduced pressure to ca. 200 ml, diluted with water (200 ml) and this mixture washed with toluene (3×100 ml). The resulting aqueous phase was acidified with concentrated hydrochloric acid to pH 4 and the white precipitate collected and dried by suction to provide the title compound (34.1 g). δ (DMSO$_{d6}$): 1.13 (3H,t), 2.56 (2H,q), 6.42 (1H,s).

(4c) 3-Ethyl-4-nitro-1H-pyrazole-5-carboxylic acid

Fuming sulphuric acid (17.8 ml) was added dropwise to stirred, ice-cooled fuming nitric acid (16.0 ml), the resulting solution heated to 50° C., 3-ethyl-1H-pyrazole-5-carboxylic acid added portionwise over 30 minutes whilst maintaining the reaction temperature below 60° C. The resulting solution was heated for 18 hours at 60° C., allowed to cool, then poured onto ice. The title compound was obtained as a brown solid (64%). δ (DMSO$_{d6}$): 1.18 (3H,t), 2.84 (2H,m), 13.72 (1H,s).

(4d) 3-Ethyl-4-nitro-1H-pyrazole-5-carboxamide

A solution of the title compound of example (4c) (15.4 g, 0.077 mol) in thionylchloride (75 ml) was heated under reflux for 3 hours and then the cool reaction mixture evaporated under reduced pressure. The residue was azeotroped with tetrahydrofuran (2×50 ml) and subsequently suspended in tetrahydrofuran (50 ml), then the stirred suspension ice-cooled and treated with gaseous ammonia for 1 hour. Water (50 ml) was added and the resulting mixture evaporated under reduced pressure to give a solid which, after trituration with water and drying by suction, furnished the title compound as a white solid (90%). δ (DMSO$_{d6}$): 1.17 (3H,t), 2.87 (2H,m), 7.40 (1H,s), 7.60 (1H,s), 7.90 (1H,s). LRMS: m/z 185 (M+1)$^+$.

(4e) 5-Ethyl-4-nitro-1-(2-pyridylmethyl)-1H-pyrazole-3-carboxamide. (Compound VIIIB)

Caesium carbonate (1.414 kg, 4.34 mol) was added to a suspension of the title compound of example (4d) (800 g, 4.34 mol) in acetonitrile (51) and the mixture warmed to 60° C. 2-Chloromethylpyridine (664.7 g, 5.23 mol) was added and the reaction heated at 70° C. for 7 hours, then water (9.5 l) added and the reaction mixture cooled to 10° C. Granulation of this mixture gave a precipitate which was filtered and dried to afford 3-ethyl-4-nitro-1-(pyridin-2-yl)methyl-pyrazole-5-carboxamide (367 g). Sodium chloride (1.58 kg) was added to the filtrate and the solution extracted with ethyl acetate (4×1.75 l). The combined organic extracts were distilled to remove approximately 10 l of solvent, toluene (5.6 l) added over 35 minutes to the hot (69–76° C.) solution and the mixture allowed to cool. The resulting suspension was granulated at <10° C. for 30 minutes, filtered, the solid washed with ethyl acetate:toluene (50:50) 600 ml) and dried (60° C.) to afford the title compound (624 g 52%) as a light brown solid. δ (DMSO$_{d6}$): 1.08 (3H,t), 3.02 (2H,q), 5.53 (2H,s), 7.34 (2H,m), 7.65 (1H,s), 7.82 (1H,m), 7.93 (1H,s), 8.52 (1H,d). LRMS: m/z 276 (M+1)$^+$.

(4f) 4-Amino-5-ethyl-1-(2-pyridylmethyl)-1H-pyrazole-3-carboxamide. (Compound IXB)

A mixture of Lindlar catalyst (2 g) and the title compound of example (4e) (20 g, 72.7 mmol) in ethanol (160 ml) was hydrogenated for 48 hours at 345 kPa (50 psi) and 50° C., then cooled and filtered. The filtrate was combined with an IMS wash (50 ml) of the filter pad and concentrated under reduced pressure to a colume of 100 ml. The remaining ethanol was removed by distillation, and replaced with ethyl acetate until a head temperature of 77° C. had been achieved. The cooled mixture was granulated at 4° C., filtered and dried to afford the title compound (13.17 g, 73%) as a light brown solid. δ (DMSO$_{d6}$): 0.90 (3H,t), 2.54 (2H,q), 4.48 (2H,s), 5.31 (2H,s), 6.89 (1H,d), 6.95 (1H,s), 7.11 (1H,s), 7.28 (1H,m), 7.74 (1H,m), 8.50 (1H,d). LRMS: m/z 246 (M+1)$^+$.

(4g) 2-Chloro-5-(4-ethyl-1-piperazinylsulphonylbenzoic acid (Compound VIIB, X=Cl)

2-Chloro-5-chlorosulphonylbenzoic acid (51.02 g, 0.2 mol) from example (2a) in water was cooled to 5° C. The pH of the reaction was adjusted to 2.2 using aqueous sodium hydroxide (5M), N-ethylpiperazine was added and the pH adjustment continued to 5.5. The reaction mixture was stirred for 12 hours at ambient temperature. The precipitated solid filtered to afford the title compound. Recrystallisation of the title compound from acetone:water affords a solid with m.p. 267–269° C. δ (DMSO): 1.00 (3H, s). 2.50 (2H, m), 2.60 (4H, m), 3.00 (4H, m), 7.75 (2H, s), 7.95 (1H, s), m/z (Found: 333 [M+H]$^+$, 100% C$_{13}$H$_{18}$ClN$_2$O$_4$S requires 333).

(4h) 4-[2-Chloro-5-(4-ethyl-1-piperazinylsulphonyl) benzamido]-5-ethyl-1-(2-pyridylmethyl)-1H-pyrazole-3-carboxamide. (Compound IIB. X=Cl)

4-Amino-5-ethyl-1-(2-pyridylmethyl)-1H-pyrazole-3-carboxamide (compound IXB) (4.02 g, 16.4 mmol) was added to a suspension of 2-chloro-5-(4-ethyl-1-piperazinylsulphonyl)benzoic acid (5.0 g,16.4 mmol), 1-(3-dimethylaminopropyl)-3-ethyl carbodiimide hydrochloride (3.15 g, 16.4 mmol) and 1-hydroxybenzotriazole (2.22 g, 16.4 mmol) in dichloromethane (50 ml). The reaction was stirred for 48 hours at ambient temperature. The reaction mixture was filtered and the solid dried to afford the title compound (2.26 g, 24.7%) as a white solid m.p. 185° C. Found: C, 53.26; H, 5.38; N,17.13. C$_{25}$H$_{30}$ClN$_7$O$_4$S requires C, 53.61; H, 5.40; N, 17.51. δ (DMSO): 0.90 (3H, t), 1.20 (3H, t), 2.30 (2H, q), 2.21 (4H, m), 2.70 (2H, q), 2.95 (4H, m), 5.50 (2H, s), 7.10 (1H, d), 7.20 (1H, m), 7.30 (2H, m), 7.85 (3H, m), 7.93 (1H, s), 8.55 (1H, d), 9.92 (1H, s). m/z (Found: 560.1835 ([M+H]$^+$, 65%). C$_{25}$H$_{31}$ClN$_7$O$_4$S requires 560.184677).

(4i) 1-Ethyl-4-{3-[3-ethyl-6,7-dihydro-7-oxo-2-(2-pyridylmethyl)-2H-pyrazolo[4,3-d]pyrimidin-5-yl]-4-propoxyphenylsulphonyl}piperazine. (Compound IB)

Potassium t-butoxide (0.90 g, 8.02 mmol) was added to a suspension of the title compound of example 4(h) (1.5 g, 2.68 mmol) in propan-1-ol (10 ml) and the mixture was heated under reflux for 48 hours. The reaction mixture was cooled and the precipitated solid was filtered and dried to afford the title compound (1.16 g, 80%). Recrystallisation of the title compound from methyl isobutyl ketone afforded a solid with m.p. 95° C. δ (CDCl$_3$): 1.00 (3H, t), 1.12 (3H, t), 1.30 (3H, t), 2.02 (2H, m), 2.40 (2H, q), 2.50 (4H, m), 3.10 (6H, m), 4.13 (2H, t), 5.70 (2H, s), 7.20 (3H, m), 7.60 (1H, m), 7.80 (1H, m), 8.55 (1H, m), 8.80 (1H, m), 10.60 (1H, s). m/z (Found: 566.257068 ([M+H]$^+$, 100%). C$_{28}$H$_{36}$N$_7$O$_4$S. requires 566.257068).

On sampling the reaction mixture using HPLC, the result suggests that the reaction pathway proceeds mainly via intermediate IVB. The invention thus provides an excellent process for preparing compounds of formula I which is safe (obviates the need to use carcinogenic alkylating reagents), is economic, utilises readily available starting materials, and which combines a novel displacement and ring closure reaction in one reaction vessel.

What is claimed is:

1. A process for the preparation of a compound of formula (IA) or (IB) below:

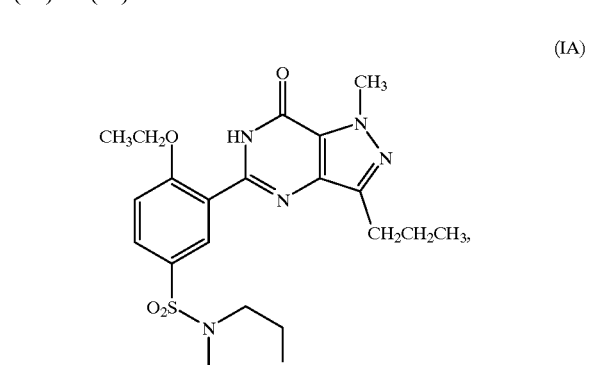

(IA)

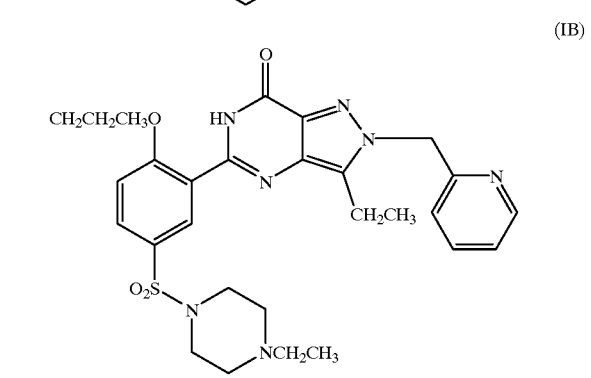

(IB)

comprising reacting a compound of formula (IIA) or (IIB) respectively

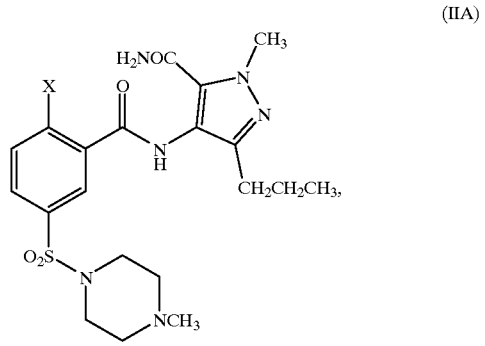

(IIA)

(IIB)

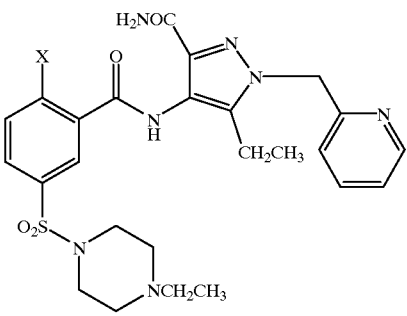

in the presence of ⁻OR, wherein R in the case of formation of compound (IA) is $CH_2CH_3$ and R in the case of formation of compound (IB) is $CH_2CH_2CH_3$, and wherein X is a leaving group.

2. A process as claimed in claim 1 wherein X is selected from the group consisting of arylsulphonyloxy, $C_1$–$C_4$ alkylsulphonyloxy, nitro or halo substituted benzenesulphonyloxy, $C_1$–$C_4$ perfluoroalkylsulphonyloxy, aroyloxy, substituted aroyloxy, $C_1$–$C_4$ perfluoroalkanoyloxy, $C_1$–$C_4$ alkanoyloxy, diazonium; $C_1$–$C_4$ primary and secondary alkoxy, oxonium, perchloryloxy, quatenaryammonium $C_1$–$C_4$ alkylsulphonuloxy, halosulphonyloxy, halonium and diarylsulphonylamino.

3. A process as claimed in claim 2 wherein X is a halo or methoxy.

4. A process as claimed in claim 3 wherein X is fluoro, chloro or methoxy.

5. A process as claimed in claim 4 wherein X is fluoro or chloro.

6. A process as claimed in claim 1 wherein ⁻OR is present with an auxiliary base.

7. A process as claimed in claim 6 wherein the auxiliary base is selected from the group consisting of sterically hindered base, a metal salt of 1-methyl piperazine, 1-ethylpiperazine, morpholine, a metal hydride, metal oxide, metal carbonate and metal bicarbonate.

8. A process as claimed in claim 7 wherein the sterically hindered base is a metal salt of a sterically hindered alcohol or amine.

9. A process as claimed in claim 8 wherein the metal salt of a sterically hindered alcohol or amine is selected from the group consisting of a secondary or tertiary $C_4$–$C_{12}$ alkanol, a $C_3$–$C_{12}$ cycloalkanol and a secondary or tertiary ($C_3$–$C_8$ cycloalkyl)$C_1$–$C_6$ alkanol, a N-(secondary or tertiary $C_3$–$C_6$ alkyl)-N-(primary, secondary or tertiary $C_3$–$C_6$ alkyl)amine, a N-($C_3$–$C_8$ cycloalkyl)-N-(primary, secondary or tertiary $C_3$–$C_6$ alkyl)amine, a di($C_3$–$C_8$ cycloalkyl)amine or hexamethyldisilazane 1,5-diazabicyclo[4,3,0]non-5-ene 1,8-diazabicyclo[5,4,0]undec-7-ene and a tertiary amine.

10. A process as claimed in claim 9 wherein the auxiliary base is a metal salt of a tertiary alkanol.

11. A process as claimed in claim 1 wherein the reaction is carried out in an inert solvent or ROH or a mixture of an inert solvent and ROH.

12. A process as claimed in claim 11 wherein the solvent is selected from the group consisting of ethanol, n-propanol, a secondary or tertiary $C_4$–$C_{12}$ alkanol, a $C_3$–$C_{12}$ cycloalkanol, a tertiary $C_4$–$C_{12}$ cycloalkanol, a secondary or tertiary ($C_3$–$C_7$ cycloalkyl)$C_2$–$C_6$ alkanol, a $C_3$–$C_9$ alkanone, 1,2-dimethoxyethane, 1,2-diethoxyethane, diglyme, tetrahydrofuran, 1,4dioxan, toluene, xylene, chlorobenzene, 1,2-dichlorobenzene, acetonitrile, dimethyl sulphoxide, sulpholane, dimethylformamide, N-methylpyrrolidin-2-one, pyridine, and mixtures thereof.

13. A process as claimed in claim 12 wherein the solvent is selected from the group consisting of ethanol, n-propanol, a tertiary $C_4$–$C_{12}$ alkanol, a tertiary $C_4$–$C_{12}$ cycloalkanol, a tertiary ($C_3$–$C_7$ cycloalkyl)$C_2$–$C_6$ alkanol, a $C_3$–$C_9$ alkanone, 1,2-dimethoxyethane, 1,2-diethoxyethane, diglyme, tetrahydrofuran, 1,4-dioxan, toluene, xylene, chlorobenzene, 1,2-dichlorobenzene, acetonitrile, sulpholane, dimethylformamide, N-methylpyrrolidin-2-one, pyridine, and mixtures thereof.

14. A process as claimed in claim 13 wherein the solvent is ethanol or propanol.

15. A process for the preparation of a compound of formula (IA) or (IB) below:

(IA)

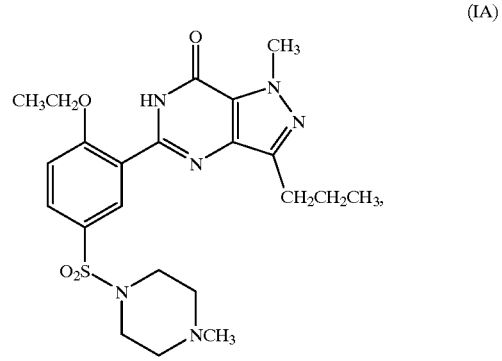

(IB)

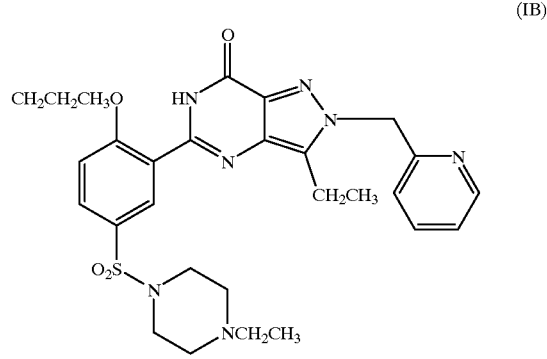

comprising reacting a compound of formula (IIA) or (IIB) respectively (IIA)

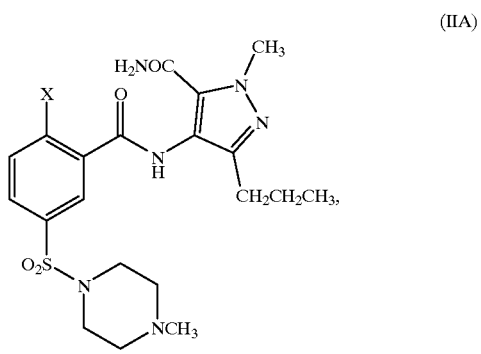

-continued

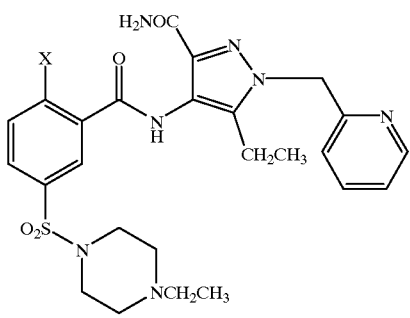
(IIB)

in the presence of ⁻OR, wherein R in the case of formation of compound (IA) is CH₂CH₃ and R in the case of formation of compound (IB) is CH₂CH₂CH₃, or ⁻OR together with an auxiliary base or ZOR together with an auxiliary base wherein ZOR is a salt of ⁻OR and Z is a cation.

16. A process as claimed in claim 15 for the production of compound (IA)

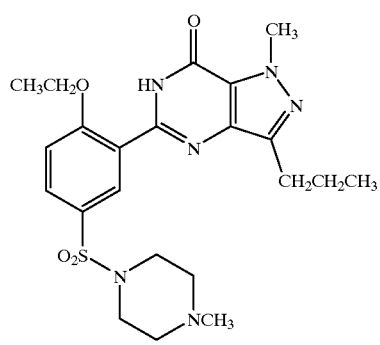
(IA)

comprising reacting compound (IIA):

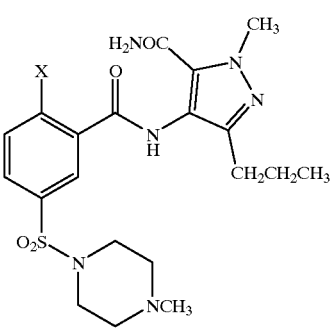
(IIA)

a) with ethanol and auxiliary base, optionally in an inert solvent; or b) with ZOEt and an auxiliary base in ethanol or an inert solvent or a mixture thereof; or c) with ZOEt and ethanol or an inert solvent or a mixture thereof wherein Z is a cation.

17. A process as claimed in claim 15 for the production of compound (IB)

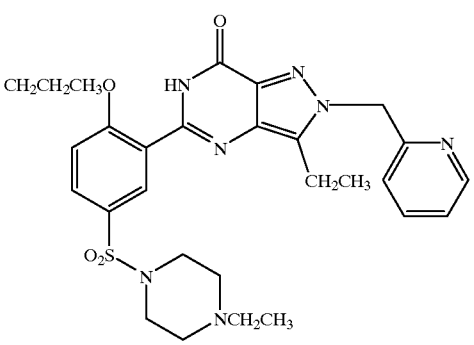
(IB)

comprising reacting compound (IIB):

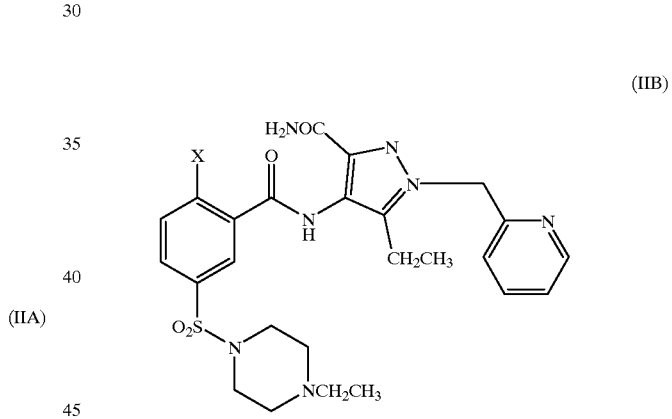
(IIB)

a) with propanol and an auxiliary base, optionally in an inert solvent; or b) with ZOPr and an auxiliary base, in propanol or an inert solvent or a mixture of both; or c) with ZOPr, and propanol or an inert solvent or a mixture of both wherein Z is a cation.

* * * * *